United States Patent
Sue

(10) Patent No.: US 6,295,988 B1
(45) Date of Patent: Oct. 2, 2001

(54) TONGUE LIFT AND LIP SEAL MOUTHPIECE

(76) Inventor: Steven K. Sue, P.O. Box 10515, Honolulu, HI (US) 96816

( * ) Notice: Subject to any disclaimer, the term of this patent is extended or adjusted under 35 U.S.C. 154(b) by 0 days.

(21) Appl. No.: 08/932,045

(22) Filed: Sep. 17, 1997

(51) Int. Cl.$^7$ ............................................. A61C 5/14
(52) U.S. Cl. ........................ 128/859; 128/860; 128/861
(58) Field of Search .................................. 128/846, 848, 128/859–862; 602/902

(56) References Cited

U.S. PATENT DOCUMENTS

| 2,483,157 | * | 9/1949 | Singer | 128/861 |
| 3,107,668 | * | 10/1963 | Thompson | 128/861 |
| 4,169,473 | | 10/1979 | Samelson . | |
| 4,672,959 | * | 6/1987 | May | 128/861 |
| 4,718,662 | * | 1/1988 | North | 128/860 |
| 4,997,182 | | 3/1991 | Kussick . | |
| 5,082,007 | * | 1/1992 | Adell | 128/859 |
| 5,117,816 | | 6/1992 | Shapiro et al. . | |
| 5,462,066 | | 10/1995 | Snyder . | |
| 5,584,687 | | 12/1996 | Sullivan et al. . | |
| 5,592,951 | | 1/1997 | Castagnaro et al. . | |
| 5,636,379 | | 6/1997 | Williams . | |

* cited by examiner

Primary Examiner—Michael A. Brown
(74) Attorney, Agent, or Firm—Siemens Patent Services

(57) ABSTRACT

An oral device for holding the tongue pressed against the roof of the mouth, thereby promoting suction closing the lips and encouraging breathing through the nose. The device has a U-shaped channel for engaging the upper teeth of the user, the channel comprising a vertical wall. A platform protects horizontally and inwardly from the U-shaped channel. This platform is located at the level of the bottom surfaces of the upper teeth, and supports the tongue. The platform bears concave indentations molded to conform to individual teeth of the user. The platform has a nominally flat bottom surface, at least one drainage hole enabling saliva to pass to the bottom of the mouth, and a slot opening to the rear of the device.

3 Claims, 2 Drawing Sheets

TONGUE LIFT AND LIP SEAL MOUTHPIECE

BACKGROUND OF THE INVENTION

1. Field of the Invention

The present invention relates to physiological devices worn within the mouth for supporting the tongue and lips in appropriate positions for promoting effective and efficient physiological functions, such as breathing and swallowing. The device cooperates with the upper teeth and provides a platform supporting the tongue. Usage of this device will encourage breathing through the nose, develop normal swallowing posture, and will open breathing passageways, so that athletic performance and alertness are enhanced, snoring is reduced, and bodily activities are generally conducted in a more efficient manner.

2. Description of the Prior Art

The tongue, lips, and other parts of the mouth exert significant influences on breathing and ancillary functions of the body. Efficiency of breathing and air flow within the mouth and other breathing passages maximizes physiological functions, such as athletic activities, and night time breathing. In particular, unimpeded air flow during sleep is characteristic of those who do not snore when sleeping. Tissues of structure associated with the mouth and breathing passages can deform over time due to age or due to various congenital or induced conditions of infirmity. These tissues may become displaced responsive to these conditions, and may come to interfere with breathing.

Prophylactic devices for reversing adverse effects of displaced tissue have been proposed in the prior art. In particular, benefit of supporting the tongue within the mouth has long been recognized as leading to improvement of various debilitating conditions. Devices which are worn in the mouth and affect position of the tongue have been proposed as leading to eliminating snoring, improving breathing, and other benefits.

U.S. Pat. No. 4,169,473, issued to Charles F. Samelson on Oct. 2, 1979, describes a device which cooperates with upper and lower teeth for support, and which has a tubular member open at one end for receiving and supporting the tongue. This device constrains the tongue to occupy a central position between the teeth, rather than supporting the tongue above the level at which upper teeth meet lower teeth, as occurs in the present invention.

A device for directing the tongue is shown in U.S. Pat. No. 4,997,182, issued to Leon Kussick on Mar. 5, 1991. This device lacks the horizontal tongue supporting member of the present invention.

U.S. Pat. No. 5,584,687, issued to Maureen P. Sullivan et al. on Dec. 17, 1996, illustrates a device intended to overcome clenching of the teeth. The subject device has right and left pads which absorb force from the teeth. These pads are connected by an arched member extending from right to left and projecting upwardly against the roof of the mouth. By contrast, the present invention has a single, U-shaped member corresponding to the pads. A horizontal member projects inwardly from the U-shaped member. The present invention thus supports the tongue at a level roughly even with and parallel to the upper teeth. By contrast, the arched member of Sullivan et al. is located above the tongue and avoids contact therewith, rather than influencing position of the tongue as occurs in the present invention.

An oral device seen in U.S. Pat. No. 5,592,951, issued to Vincent Castagnaro et al. on Jan. 14, 1997, provides U-shaped channels for engaging both upper and lower teeth, and an arched member projecting inside of and spanning these channels. By contrast, the member projecting inside the tooth engaging channel of the present invention is flat and horizontal. Also, the tooth engaging member of the present invention engages only the upper teeth, whereas the device of Castagnaro et al. engages both upper and lower teeth.

None of the above inventions and patents, taken either singly or in combination, is seen to describe the instant invention as claimed.

SUMMARY OF THE INVENTION

The present invention provides a device for supporting the tongue in a suitable position for maintaining sealing of the lips and tongue during ordinary breathing. This is a position which is naturally achieved under ordinary conditions, but from which the tongue and tissue at the epiglottis may depart due to adverse prevailing conditions of age and infirmity. The novel device enables ordinary air flow to prevail despite conditions contravening ideal conditions.

Benefits accruing from the invention include causing the user to become accustomed to breathing through the nose, thereby enhancing alertness and athletic performance, opening airways generally. Also, nasal congestion is relieved, deep breathing is promoted, stress is reduced, heart beat rate is decreased, and body and mind breathing are coordinated. In the case of persons breathing through the nose, normal swallowing patterns for tongue thrusters are developed, and snoring is reduced. Correction of tongue thrusting will aid in speech therapy, promote better growth and development of jaws, and will improve stability of orthodontic treatment results.

To these ends, the present invention comprises a U-shaped channel cooperating with the upper teeth. A platform projects horizontally from the interior surfaces of the U-shaped channel at a level corresponding to that even with the bottom surfaces of the teeth. Optionally, a drain hole is formed in the platform to relieve buildup of saliva. The tongue rests on the platform, and is held in a position against the roof of the mouth, thereby establishing a mild suction between the tongue and the roof of the mouth. This occurrence assures sealing of the lips, thereby promoting breathing through the nose. The device is formed from a flexible material. A slot formed in the platform opens to the rear, to relieve undue intrusion into the soft tongue. This feature as well as flexibility contribute to comfort.

If the device is fabricated sufficiently strongly, it may be employed as a guard in athletic activities.

Accordingly, it is a principal object of the invention to provide a mouthpiece for holding the tongue against the roof of the mouth.

It is another object of the invention to promote breathing through the nose.

It is a further object of the invention to encourage proper swallowing posture and to reduce snoring in persons breathing through the mouth.

Still another object of the invention is to open airways generally.

An additional object of the invention is to relieve nasal congestion, to promote deep breathing, to reduce stress and heart beat rate, and to improve coordination of body and mind breathing.

An additional object of the invention is to enhance breathing volume, alertness, and athletic performance and endurance.

It is again an object of the invention to provide at least one drain hole formed in the platform supporting the tongue.

Yet another object of the invention is that the oral device be comfortable to wear.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
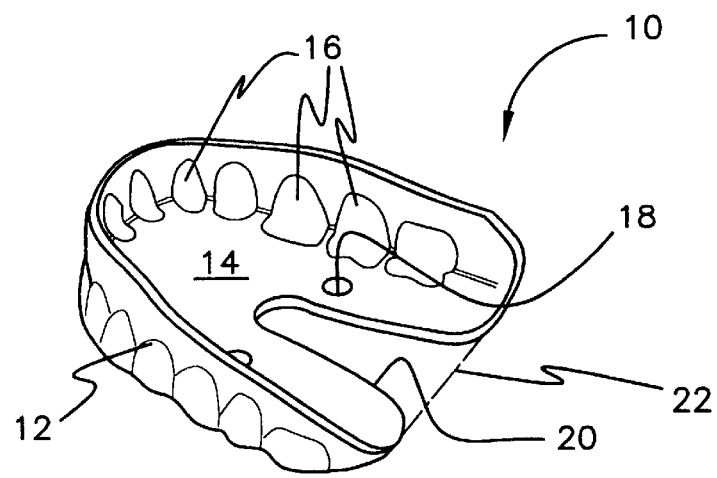
FIG. 1 is a rear perspective view of a first embodiment of the invention.

FIG. 1 of the drawings shows a first embodiment of the novel oral device 10. Device 10 is seen to comprise a channel having a generally U-shaped, vertical peripheral wall 12 disposed to partially surround a U-shaped row of teeth (not shown). Partial surroundment signifies that wall 12 makes substantial, but not fully surrounding, contact with the teeth. A platform 14 projects horizontally and inwardly from wall 12 at the bottom of wall 12, platform 14 being connected to the channel at a level even with that of the bottom surfaces of the upper teeth. Therefore, wall 12 may be said to project upwardly from platform 14.

Concave indentations 16 are formed in both wall 12 and in platform 14. Indentations 16 correspond to configuration of individual teeth of the row partially surrounded by wall 12. This configuration assures close cooperation between device 10 and the teeth, thereby enhancing adherence of device 10 to the mouth by engaging the teeth. Indentations 16 are readily molded by those skilled in the dental arts, and the process of creating indentations 16 closely conforming to the teeth of a particular person need not be set forth in detail herein.

Platform 14 has at least one, and in the depiction of FIG. 1, two, drainage holes 18 for avoiding accumulation of saliva on platform 14. Holes 18 also offer tactile stimulus confirming correct positioning of the tongue, although effectiveness of this stimulus would be enhanced with larger holes, such as holes 58 of FIG. 3. Holes 18 extend vertically and entirely through platform 14. Platform 14 also has a slot 20 formed therein. Slot 20 opens to the rear of device 10. For purposes of this discussion, the front of device 10 is that side disposed towards the front of the user's mouth, and the rear faces the rear of the user's head. Slot 20 relieves a straight line that would be assumed by the rearmost vertical surface of Platform 14 if slot 14 were not present. This straight line is represented by projection line 22. The purpose of slot 20 is to allow a portion of the tongue to depend from the tip of the tongue without having to conform to line 22. Of course, it should be understood that the holes 18 could be eliminated. Holes 18 are not absolutely crucial to the functioning of the invention. However, it is important that the minimum distance that platform 14 extends back into the mouth is a line drawn from the user's bicuspid teeth, the third tooth counting back from the incisors.

Figure 2:
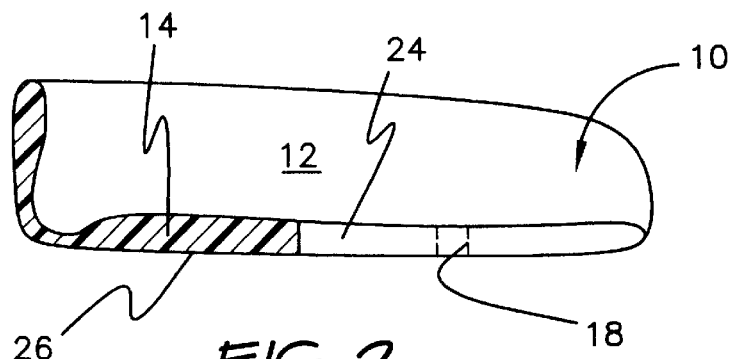
FIG. 2 is a side cross sectional view of FIG. 1.

The depiction of FIG. 2 also reveals a nominally flat upper surface 24 and nominally flat lower surface 26 of platform 14. Surfaces 24 and 26 are nominally flat in that a perfect planar surface is not required. It is merely desired that the tongue and other tissues of the mouth pass relatively unobstructed over these surfaces 24, 26. It is more critical that surface 24 be flat, for supporting the tongue in a flat, spread condition in its position against the roof of the mouth. Flat surfaces 24 and 26, as well as slot 20 and relief from saliva accumulation afforded by holes 18, enhance comfort of device 10.

Comfort is still further enhanced by forming device 10 from a flexible, partially rigid synthetic material. The material is sufficiently flexible to bend under manual pressure, but partially rigid in that it will hold its configuration absent manual or equivalent pressure acting to deform its configuration as shown in the drawings. Suitable materials may be selected from silicones and synthetic resins, including those conventionally employed to form castings and impressions for dental and other purposes.

Figure 3:
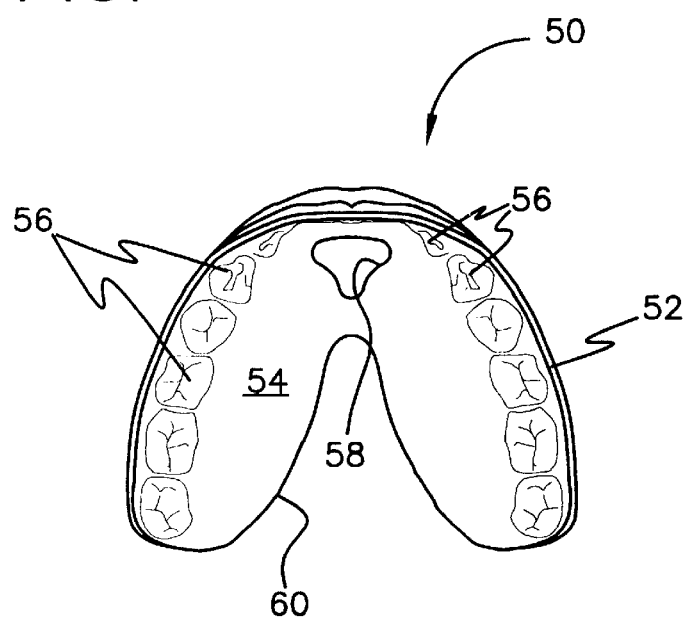
FIG. 3 is a top plan view of a second embodiment of the invention.

FIG. 3 illustrates another arrangement for providing drainage of saliva. Oral device 50 is similar to the embodiment of FIG. 1 in having a wall 52, platform 54, indentations 56, and slot 60 all corresponding to similar structure present in the embodiment of FIG. 1. However, in place of the two holes 18 of FIG. 1, device 50 has a single hole 58. Hole 58 is relocated towards the front of platform 54, compared to the embodiment of FIG. 1. Also, hole 58 is larger than either hole 18. Of course, any number of drainage holes may be provided, and may be of any desired location and size.

Figure 4:
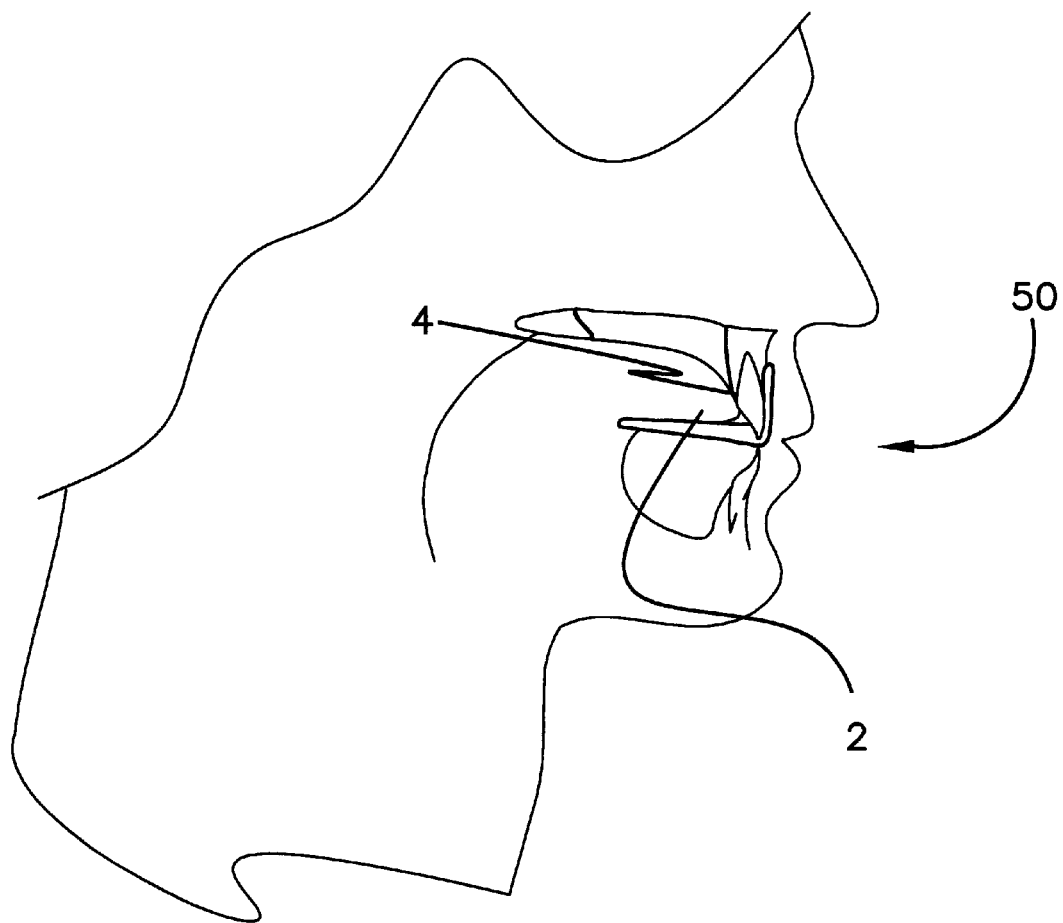
FIG. 4 is a diagrammatic, environmental, side cross sectional view of the invention.

FIG. 4 illustrates support of the tongue at the roof of the mouth with the anterior tip 2 of the tongue located at the incisal papilla or at the hard palate 4. The tongue is supported by device 10 or 50. Constraining the tongue in the manner depicted in FIG. 4 causes a mild or subtle suction maintaining the tongue in place and urging the lips to remain closed. This condition promotes breathing through the nose. The degree of suction desired will influence the number, size, and placement of drainage holes.

The present invention is susceptible to variations and modifications which may be introduced without departing from the inventive concept. Illustratively, it would be possible to truncate the full U-shaped configuration of the channel by engaging fewer than all of the upper teeth. However, the savings in material and complexity is insignificant, and further entails loss of engaging contact with the teeth such that successful engagement could be threatened. In addition, the front portion of the U shape provides a wall interfering with excessive forward projection of the tongue, and therefore will contribute to successful use in some individuals who might otherwise defeat successful use by forward projection of the tongue. It is preferred, therefore, to configure the channel as fully U-shaped and configured to partially surround all teeth of one jaw.

While device 10 could be modified to obtain anchorage within the mouth by engagement of the lower teeth, it is greatly preferred to engage the upper teeth. The preferred arrangement assures more compact construction of device

10, and also allows some mobility of the lower jaw without impairing successful constraint of the tongue in the preferred position.

It is to be understood that the present invention is not limited to the embodiments described above, but encompasses any and all embodiments within the scope of the following claims.

I claim:

1. A fitted oral appliance for placing and maintaining a user's tongue in contact with both the hard and soft palate of the user, comprising:

a) a substantially U-shaped channel molded to accept at least a tip portion of the user's upper teeth, thereby retaining said oral appliance in a predetermined position in the user's mouth;

b) a continuous, generally vertical peripheral wall around an outer portion of said U-shaped channel, said peripheral wall molded to and further enclosing the peripheral portion of the user's upper teeth and the user's gums; and c) a thin, substantially horizontal planar member forming a platform continuously attached to and extending along an inner edge of said U-shaped channel, said platform being at substantially the same level as said tips of said user's upper teeth, said platform having an inner edge defining a varying platform width relative to said inner portion of said U-shaped channel, said inner edge defining a substantially V-shaped opening therein, the vertex of said V-shaped opening being proximate the lingual surface of said user's incisors;

whereby said user's tongue is held in position substantially flat against the roof of the user's mouth by said platform.

2. The fitted oral appliance for placing and maintaining a user's tongue in contact with both the hard and soft palate of the user as recited in claim 1, wherein said platform includes at least one aperture extending completely therethrough.

3. The fitted oral appliance for placing and maintaining a user's tongue in contact with both the hard and soft palate of the user as recited in claim 1, wherein said oral appliance comprises a partially rigid synthetic material.

* * * * *